United States Patent
Maraschino

Patent Number: 5,847,249
Date of Patent: Dec. 8, 1998

[54] APPARATUS AND PROCESS FOR CATALYTIC DISTILLATIONS

[75] Inventor: Mario J. Maraschino, Kingwood, Tex.

[73] Assignee: Catalytic Distillation Technologies, Pasadena, Tex.

[21] Appl. No.: 901,169

[22] Filed: Jul. 28, 1997

[51] Int. Cl.⁶ .............. C07C 7/163; C07C 5/03; B01J 8/04; B01D 3/34
[52] U.S. Cl. .............. 585/259; 203/28; 203/29; 203/DIG. 6; 208/347; 208/350; 422/191; 422/193
[58] Field of Search .............. 203/28, 29, DIG. 6; 208/347, 350; 422/191, 193; 585/259

[56] References Cited

U.S. PATENT DOCUMENTS

| | | | |
|---|---|---|---|
| 4,950,834 | 8/1990 | Arganbright et al. | 585/446 |
| 4,994,098 | 2/1991 | Agarwal et al. | 62/22 |
| 5,105,024 | 4/1992 | McKay et al. | 568/697 |
| 5,308,592 | 5/1994 | Yang et al. | 422/191 |
| 5,321,163 | 6/1994 | Hickey et al. | 568/59 |
| 5,431,888 | 7/1995 | Hickey et al. | 422/191 |
| 5,595,634 | 1/1997 | Hearn et al. | 203/29 |
| 5,628,880 | 5/1997 | Hearn et al. | 203/29 |

*Primary Examiner*—Bekir L. Yildirim
*Attorney, Agent, or Firm*—Kenneth H. Johnson

[57] ABSTRACT

A process for selectively treating the components in a multi-component stream in a distillation column reactor. Additional catalytic distillation structures are placed as a secondary bed in the distillation column, either above or below the primary bed, and the selected component withdrawn after reaction in the primary bed to prevent its entry into the secondary bed.

16 Claims, 2 Drawing Sheets

APPARATUS AND PROCESS FOR CATALYTIC DISTILLATIONS

BACKGROUND OF THE INVENTION

1. Field of the Invention

The present invention relates to an apparatus and process for improving the flexibility of operation of reactive distillation processes.

2. Related Art

The use of catalyst in a distillation column to concurrently carry out chemical reactions and separate the reaction products has been practiced for some time. This use of a catalytic distillation column reactor lends itself particularly well for reversible reactions in the liquid phase. See for example U.S. Pat. No. 4,336,407 (etherification), U.S. Pat. No. 4,482,775 (isomerization), U.S. Pat. No. 4,242,530 (separation of isobutene from $C_4$ streams) and U.S. Pat. No. 4,551,567 (deetherification). The combination is useful because the reactants in the liquid phase are quickly separated from the reaction products due to boiling point differences by fractional distillation. Thus the reverse reaction is suppressed.

Several different arrangements have been disclosed to achieve the desired result. For example British Patents 2,096,603 and 2,096,604 disclose placing the catalyst on conventional trays within a distillation column. A series of U.S. patents, including those listed above, commonly assigned with the instant invention discloses using the catalyst as part of the packing in a packed distillation column. More particularly U.S. Pat. Nos. 4,443,559 and 4,215,011 exemplify the latter. The use of multiple beds in a reaction distillation tower is also known and illustrated, for example in U.S. Pat. Nos. 4,950,834; 5,321,163; and 5,595,634.

In reactive distillations, such as catalytic distillation, as in any other distillation there is not a rigid cut off between the component. Reactions carried on in specified portions of the column using some constituents may leave undone other desirable treatment of other portions of the column constituents.

For example, mixed refinery streams often contain a broad spectrum of olefinic compounds. This is especially true of products from either catalytic cracking or thermal cracking processes. These unsaturated compounds comprise ethylene, acetylene, propylene, propadiene, methyl acetylene, butenes, butadiene, amylenes, hexenes etc. Many of these compounds are valuable, especially as feed stocks for chemical products. Olefins having more than one double bond and the acetylenic compounds (having a triple bond) have lesser uses and are detrimental to many of the chemical processes in which the single double bond compounds are used, for example polymerization. Sulfur and nitrogen compounds, among others, are frequently desirably removed also and they may be effectively removed from a portion of the column constituents but because of different boiling points for other portions of the column constituents and the contaminants therein, not all of the contaminants may be removed.

The problem actually arises from the major benefit of reactive distillation, i.e., the ability to isolate portions of column constituents and hold these in the catalyst bed for whatever purpose desired. Other constituents will pass through the catalyst bed with little effective contact.

For example, $C_4$ hydrocarbon cut will contain $C_3$ and $C_5$ and possibly even other hydrocarbon species. Thus, a reaction involving the $C_4$'s will result in a $C_3$ portion and a $C_5$ portion that by the very nature of the reactive distillations are not handled by catalytic reaction, e.g., the $C_3$'s are vaporous and may pass through the catalyst bed without sufficient contact time, similarly the $C_5$'s are not likely to be vaporized in adequate quantities to be in substantial contact with the catalyst.

In this illustration consider the reactions as etherification of tertiary butene in the $C_4$ stream with methanol. The conventional manner of operation would be to recover the ether and all heavies as bottoms and the unreacted $C_4$'s (alkanes as n-butenes as overheads with the $C_3$.

In this illustration a problem is the $C_3$ portion (a small fraction) will likely contain methyl acetylene and propadiene (MAPD) which is detrimental to many subsequent uses to which the overhead raffinate may be part.

In a further example, using catalytic distillation in a $C_4/C_5$ splitter to remove vinyl acetylene and ethyl acetylene, over 90% of both were removed from the $C_4$ portion by selective hydrogenation, but only 40% of the MA and 20% of the PD was removed because they were constituents of a column component ($C_3$'s) which was lighter than the $C_4$ column component.

The present invention provides apparatus and process to address the reactive distillation treatment of the total constitution of the distillation column reactor.

SUMMARY OF THE INVENTION

Briefly the present invention includes an apparatus for conducting reactive distillations comprising a distillation column, at least one primary catalyst bed for carrying out a first specific reaction, said primary catalyst bed being positioned in said distillation column to provide a first reaction zone for materials in said distillation column, a side draw associated with said reaction zone to remove the reaction product therein from said distillation column and at least one secondary catalyst bed adjacent to said primary catalyst bed, said secondary catalyst bed to provide a second reaction zone for materials remaining in said distillation column after said first reaction zone. The process carried out in the apparatus is also part of the present invention.

There may be distillation structures or trays between the primary and secondary beds. There also may be several groupings of primary and secondary beds along a column. The secondary beds may also have a side draw associated with the reaction zone.

The present process comprises catalytically treating selective components of a multi-component stream in a distillation column reactor in a primary catalyst bed. A secondary catalyst bed is positioned in the distillation column, either above or below the primary bed, and the selected component withdrawn after reaction in the primary bed to prevent its entry into the secondary bed. In this way lighter or heavier boiling components can be exposed to additional catalyst and be purified or treated by further reaction to convert impurities without subjecting the selected component from further reaction.

In some embodiments the secondary catalyst bed may be the main reaction bed for particular reaction product.

DETAILED DESCRIPTION OF THE INVENTION

Figure 1:
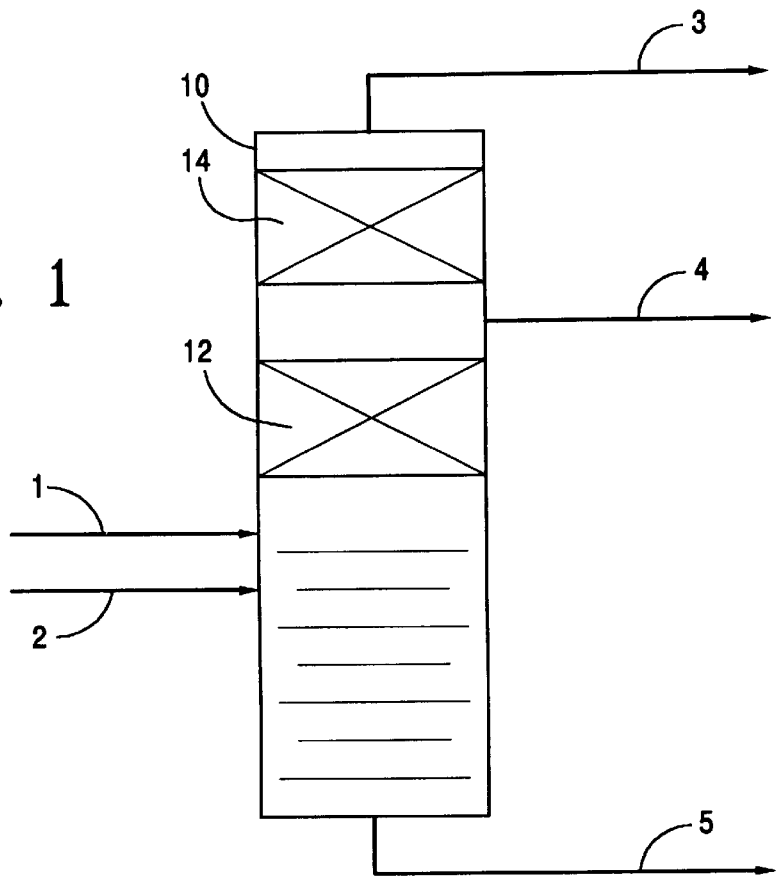
FIG. 1 is a simplified process flow diagram of one embodiment of the invention.

In catalytic distillation columns multi-component mixtures are typically used as feed stock. Usually the mixtures will span several different carbon number ranges. Normally, compounds in one carbon number range (such as $C_4$'s in a $C_4/C_5$ splitter) will function as the light key grouping in the column. Thus compounds one carbon number greater (such as $C_5$'s in a $C_4/C_5$ splitter) will serve as the heavy key grouping for the column. The components in the light key grouping build up by about twofold to threefold in the rectification zone above the liquid feed entry point. Likewise, the components in the heavy key grouping build up in concentration in the stripping zone below the liquid feed entry point. Any component lighter than the light key grouping ($C_3$'s in the context of a $C_4/C_5$ splitter) are present at much higher concentration in the rectification vapor than in the rectification liquid. These lighter than light key components will thus concentrate up at the extreme tip of the column where so-called "end effects" are initiated, i.e., in the vicinity of the topmost one or two theoretical stages. In an analogous fashion, components that are heavier than the heavy key grouping ($C_6$'s in a $C_4/C_5$ splitter) will appear diluted in the stripping section of the column because they become concentrated in the extreme bottom of the column where the "end effects" are initiated, i.e., in the vicinity of the bottommost one or two theoretical stages.

When the process is specific for treating one of the key groupings only then is there generally no problem. However when the desire is to treat the components that are lighter than light key grouping or heavier than the heavy key grouping, then problems arise. Because in both cases the lighter and heavier than key components are in dilute phases in the catalyst beds there is a lower driving force for the reaction. Simply increasing the height of the column and adding additional catalyst above or below the reaction section exposes the key grouping to the catalyst for greater residence times which can alter the product mix, especially in selective hydrogenations.

The solution has been found to add the extra height and catalyst but remove the key groupings as a side draw either below or above the added catalyst. This prevents the key grouping components from being exposed to the extra catalyst bed.

Hydrogenation is the reaction of hydrogen with a carbon-carbon multiple bond to "saturate" the compound. This reaction has long been known and is usually done at super atmospheric pressures and moderate temperatures using a large excess of hydrogen over a metal catalyst. Among the metals known to catalyze the hydrogenation reaction are platinum, rhenium, cobalt, molybdenum, nickel, tungsten and palladium. Generally, commercial forms of catalyst use supported oxides of these metals. The oxide is reduced to the active form either prior to use with a reducing agent or during use by the hydrogen in the feed. These metals also catalyze other reactions, most notably dehydrogenation at elevated temperatures. Additionally they can promote the reaction of olefinic compounds with themselves or other olefins to produce dimers or oligomers as residence time is increased.

Selective hydrogenation of hydrocarbon compounds has been known for quite some time. Peterson, et al in "The Selective Hydrogenation of Pyrolysis Gasoline" presented to the Petroleum Division of the American Chemical Society in September of 1962, discusses the selective hydrogenation of $C_4$ and higher diolefins. Boitiaux, et al in "Newest Hydrogenation Catalyst", *Hydrocarbon Processing*, March 1985, presents a general, non enabling overview of various uses of hydrogenation catalysts, including selective hydrogenation of a propylene rich stream and other cuts. Conventional liquid phase hydrogenations as presently practiced require high hydrogen partial pressures, usually in excess of 200 psi and more frequently in a range of up to 400 psi or more. In a liquid phase hydrogenation the hydrogen partial pressure is essentially the system pressure.

Conventional items such as reboilers, condensers, valves and the like have been omitted, but their functioning and positioning are merely routine in the art.

EXAMPLE 1

Referring now to FIG. 1 a process flow diagram for the removal of vinyl acetylene, ethyl acetylene, methyl acetylene and propadiene from a $C_3$–$C_4$–$C_5$ system, in a distillation column reactor 10 acting as a $C_4/C_5$ splitter is shown. Under normal circumstances both the $C_3$ and $C_4$ products would be taken overheads. However, under conditions suitable for removing 99% of the vinyl acetylene and 90% of the ethyl acetylene, all of the $C_3$'s, including the methyl acetylene and propadiene would be at much higher concentration in the vapor and relatively much lower concentration in the liquid phase. This would result in removal of only about 40% of the methyl acetylene and about 20% of the propadiene.

To achieve the desired goal, two beds of catalyst 12 and 14 are placed in the rectification section of the distillation column reactor 10. The liquid feed is fed via flow line 1 to the distillation column reactor 10 just below the lower bed 12. Hydrogen is fed below the lower bed 12 as needed via flow line 2. The $C_4$'s are concentrated in the lower bed 12 where the vinyl acetylene and ethyl acetylene are selectively hydrogenated. The $C_3$'s are concentrated in the upper bed 14 where the methyl acetylene and propadiene are selectively hydrogenated. The treated $C_3$'s are removed as overheads via flow line 3. A side draw on the tray just below the upper bed 14 removes all of the $C_4$'s and a portion of the $C_3$'s via flow line 4 to insure that all of the $C_4$'s are removed. The $C_5$'s are removed as bottoms via flow line 5. Overall the additional treatment-section catalytic distillation bed 14 working together with the regular catalytic distillation bed 12 allows for a nominal 70–80% overall removal of the methyl acetylene and propadiene along with the target removal of the vinyl acetylene (99%) and ethyl acetylene (90%).

EXAMPLE 2

Figure 2:
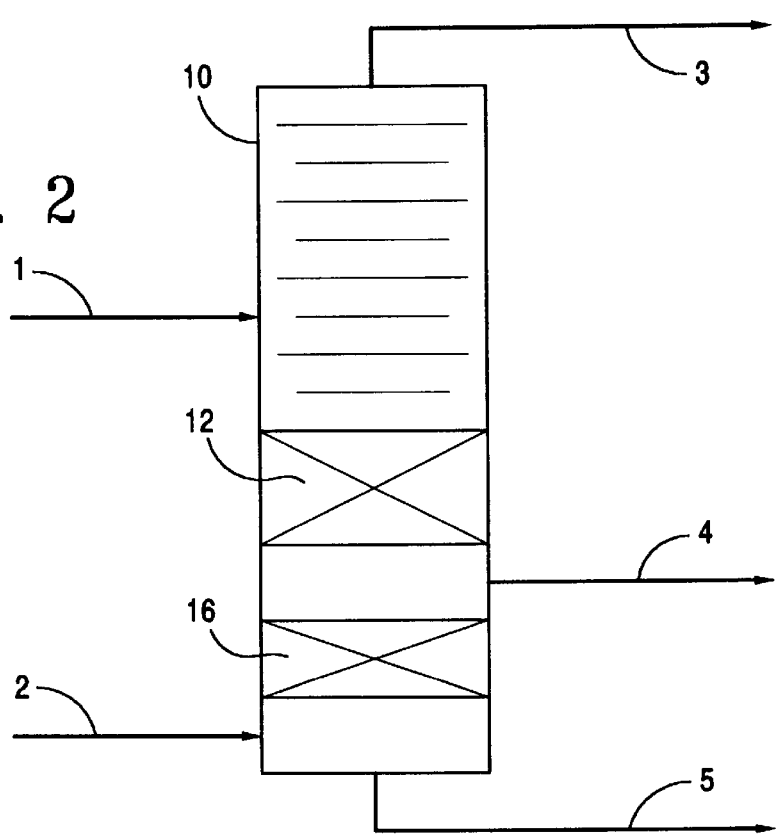
FIG. 2 is a simplified process flow diagram of a second embodiment of the invention.

Referring now to FIG. 2 a process flow diagram for the removal of butadienes and pentadienes from a $C_3$–$C_4$–$C_5$ system, in a distillation column reactor 10 acting as a $C_3/C_4$ splitter is shown. The $C_3$ fraction is not to be treated at all to prevent propylene losses. Under normal circumstances both the $C_4$ and $C_5$ components would be taken as bottoms. However, under conditions suitable for removing 90–95% of the butadienes all of the $C_5$'s would be in the heavier than heavy key range and thus diluted in the liquid phase passing over the catalyst resulting in only about 40% conversion of the pentadienes.

To achieve the desired goal, two beds of catalyst 12 and 16 are placed in the stripping section of the distillation column reactor 10. The liquid feed is fed via flow line 1 to the distillation column reactor 10 well above the top bed 12 to prevent any of the $C_3$'s from contacting the catalyst. The $C_3$'s are removed as overheads via flow line 3. Hydrogen is fed below the lower bed 16 as needed via flow line 2. The $C_4$'s are concentrated in the upper bed 12 where the butadienes are converted. The $C_5$'s are concentrated in the lower bed 16 where the pentadienes are selectively hydrogenated. The treated $C_5$'s are removed as bottoms via flow line 5. A side draw on the tray just below the upper bed 12 removes all of the $C_4$'s via flow line 4 and a portion of the $C_5$'s to insure that all of the $C_4$'s are removed. Overall the additional treatment-section catalytic distillation bed 16 working together with the regular catalytic distillation bed 12 allows for a nominal 80–85% overall removal of the pentadienes along with 90–95% of the butadienes.

EXAMPLE 3

In this example a secondary catalyst bed for one product is the primary catalyst bed for a second product. The feed is a crude fraction containing atmospheric gas oil, diesel, kerosene and naphtha. The reaction for the various constituents is hydrodesulfurization carried out in a reactive distillation column.

Figure 3:
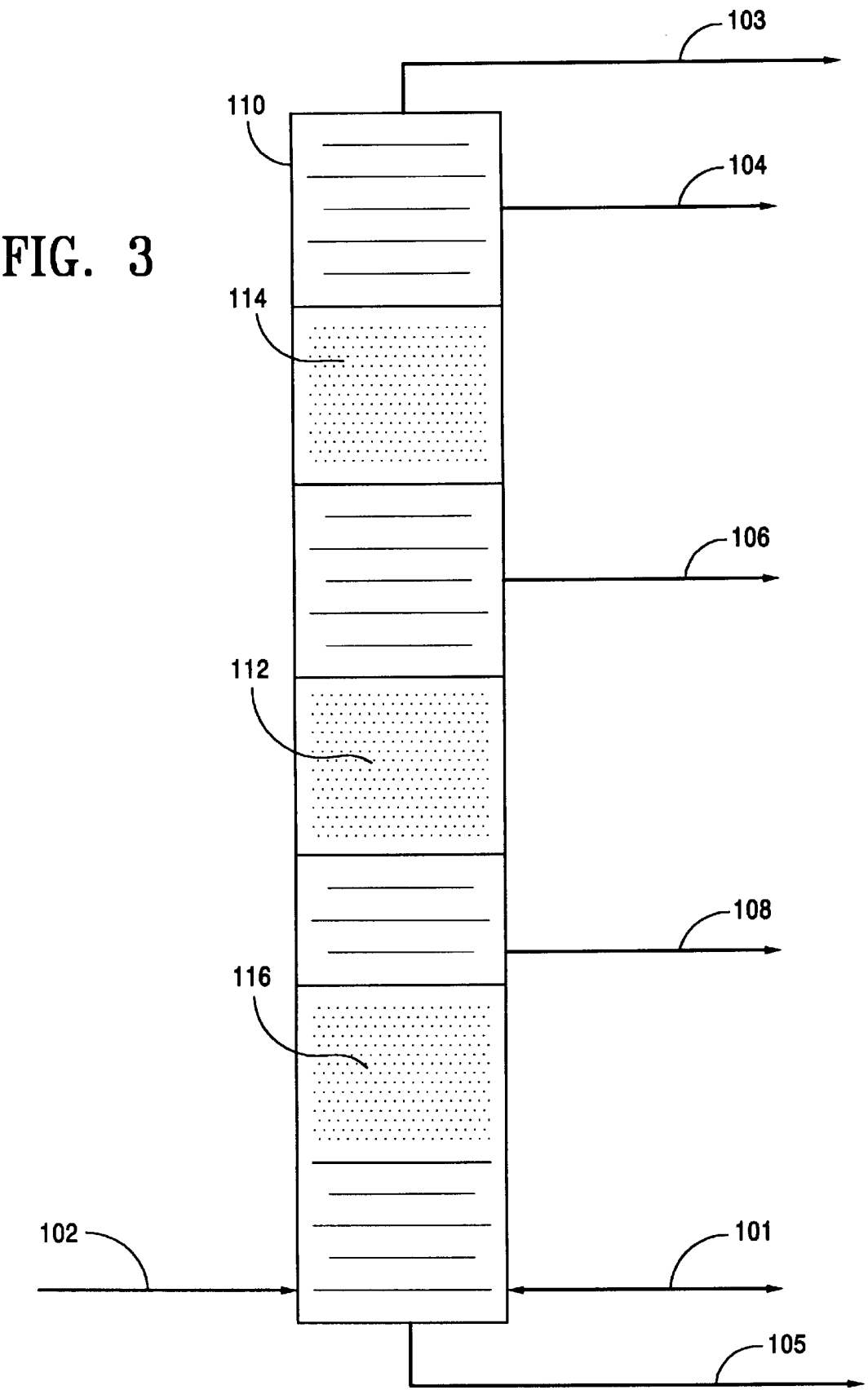
FIG. 3 is a simplified process flow diagram of an embodiment employing three catalyst beds for treating a crude fraction.

Referring to FIG. 3, the catalytic distillation column 110 contains three catalyst beds with the hydrogen and the crude petroleum for processing is fed at the bottom of the column 110 through line 102 and 101 respectively. The atmospheric gas oil is removed as a bottoms via 105. Other lighter fractions are vaporized up into the column.

The first catalyst bed 116 is used with a hydrodesulfurization catalyst prepared as a distillation structure for the hydrodesulfurization of the diesel cut. The desulfurized diesel is removed via side draw 108, however lower boiling sulfur compounds would rapidly pass through this bed while the sulfur compounds boiling in the diesel range would have been substantially removed.

In the second catalyst bed 112 which is the secondary bed to primary bed 116, hydrodesulfurization catalyst is prepared as a distillation structure. The hydrocarbon and organic sulfur compounds boiling in the kerosene range are hydrotreated to remove sulfur compounds which were not treated in the catalyst bed 116. In so doing organic sulfur compounds boiling in the kerosene range are eliminated and desulfurized kerosene is removed via side draw 106.

Thus for kerosene product, the 112 bed becomes the primary bed while also being the secondary bed for 116 diesel product.

The catalyst bed 114 is the secondary bed for the 112 bed (and at the same time the primary bed for the heavy naphtha in side draw 104. Lighter organic sulfur compounds that have bypassed the two earlier beds are now hydrodesulfurized in bed 114 which has the hydrodesulfurization catalyst in the form of distillation structure. The heavy naphtha may be removed overhead or if the sulfur content is a problem a fourth catalyst bed with the appropriate catalyst as a distillation structure can be inserted in the column above the side draw 104 and thereby become the secondary catalyst bed to the 114 catalyst bed (and the primary bed for overhead 103). Because of the catalyst beds, the present column will be substantially longer than the prior art non-catalytic columns, however, by processing multiple streams in the one unit, several separate downstream treatment units are eliminated.

The invention claimed is:

1. A process for selectively treating the key component of a multi-component stream having a key component, a lighter than key component and a heavier than key component, in a distillation column reactor, comprising:

(a) feeding the multi-component stream into a distillation column reactor having at least two catalytic distillation zones, one above the other, one of said zones being designated the primary zone and the other being designated the secondary zone;

(b) treating the key component in the primary zone;

(c) withdrawing the treated key component from between said zones; and (d) treating one of the other components in said secondary zone.

2. The process according to claim 1 wherein said secondary zone is located above said primary zone in said distillation column and said lighter than key component is treated in said secondary zone.

3. The process according to claim 1 wherein said secondary zone is located below said primary zone in said distillation column and said heavier than key component is treated in said secondary zone.

4. The process according to claim 1 wherein said multi-component stream comprises a $C_3/C_4/C_5$ stream containing olefins, di-olefins and acetylenes and the key component to be treated is the $C_4$'s to remove vinyl and ethyl acetylenes while leaving butadienes and butenes, and said secondary zone is above said primary zone to treat the $C_3$'s to remove methyl acetylene and propadiene.

5. The process according to claim 1 wherein said multi-component stream comprises a $C_3/C_4/C_5$ stream containing olefins, di-olefins and acetylenes and the key component to be treated is the $C_4$'s to remove butadienes and said secondary zone is below said primary zone to treat the $C_5$'s to remove dienes.

6. The process according to claim 1 wherein said multi-component stream comprises diesel, kerosene and naphtha and a first key component to be treated is diesel to remove organic sulfur compounds by hydrogenation in a primary zone, a first secondary zone being above the primary zone to treat the kerosene to remove organic sulfur compounds by hydrogenation and hydrogen is supplied at least below said primary bed.

7. The process according to claim 6 wherein a second key component to be treated is kerosene, there being a second secondary zone above said first secondary zone to treat naphtha to remove organic sulfur compounds by hydrogenation.

8. The process according to claim 7 wherein treated diesel is withdrawn between said primary zone and said first secondary zone and treated kerosene is withdrawn between said first secondary zone and said second secondary zone.

9. The process according to claim 1 having multiple key components, multiple lighter than key components and multiple heavier than key components.

10. A process for the selective hydrogenation of acetylenes and propadiene in a mixed $C_3/C_4/C_5$ stream comprising the steps of:

(a) feeding hydrogen and the mixed $C_3/C_4/C_5$ mixed stream into a distillation column reactor into a feed zone below the rectification zone;

(b) contacting the $C_4$ boiling range materials with a hydrogenation catalyst in a first distillation reaction zone located in the lower portion of the rectification zone to selectively hydrogenate the acetylenes contained therein;

(c) contacting the methyl acetylene and propadiene contained in the $C_3$'s with a hydrogenation catalyst in a second distillation reaction zone located in the upper portion of the rectification zone to selectively hydrogenate the acetylene and propadiene;

(d) withdrawing hydrogenated $C_4$ product in a side draw from between said first and second distillation zones;

(e) withdrawing hydrogenated $C_3$ product and unreacted hydrogen as overheads from said distillation column reactor; and (f) withdrawing $C_5$'s as bottoms from said distillation column reactor.

11. The process according to claim 10 wherein the $C_3$'s in said overheads are condensed and a portion of said condensed overheads are returned to said distillation column reactor as reflux.

12. The process according to claim 10 wherein a portion of the $C_3$'s are removed along with the hydrogenated $C_4$ product to assure that no $C_4$'s enter said second distillation reaction zone.

13. A process for the selective hydrogenation of butadienes and pentadienes contained within a mixed $C_3/C_4/C_5$ stream comprising the steps of:

(a) feeding the mixed $C_3/C_4/C_5$ mixed stream into a distillation column reactor into a feed zone above the stripping zone;

(b) feeding hydrogen into said distillation column reactor below the stripping zone;

(c) contacting the $C_4$ boiling range material with a hydrogenation catalyst in a first distillation reaction zone located in the upper portion of the stripping zone to selectively hydrogenate the butadienes contained therein;

(d) contacting the $C_5$ boiling range material with a hydrogenation catalyst in a second distillation reaction zone located in the lower portion of the stripping zone to selectively hydrogenate the pentadienes contained therein;

(e) withdrawing hydrogenated $C_4$ product in a side draw from between said first and second distillation zones;

(f) withdrawing hydrogenated $C_5$ product from said distillation column reactor as bottoms; and (g) withdrawing untreated $C_3$'s and unreacted hydrogen from said distillation column reactor as overheads.

14. The process according to claim 13 wherein the $C_3$'s in said overheads are condensed and a portion of said condensed overheads are returned to said distillation column reactor as reflux.

15. The process according to claim 13 wherein a portion of the $C_5$'s are removed along with the hydrogenated $C_4$ product to assure that no $C_4$'s enter said second distillation reaction zone.

16. An apparatus for conducting reactive distillations comprising a distillation column, at least one primary catalyst bed for carrying out a first specific reaction, said primary catalyst bed being positioned in said distillation column to provide a first reaction zone for materials in said distillation column, a side draw associated with said reaction zone to remove the reaction product therein from said distillation column and at least one secondary catalyst bed adjacent to said primary catalyst bed, said secondary catalyst bed to provide a second reaction zone for materials remaining in said distillation column after said first reaction zone.

* * * * *